(12) United States Patent
Newman et al.

(10) Patent No.: US 6,626,925 B2
(45) Date of Patent: Sep. 30, 2003

(54) SHIELDED SURGICAL SCALPEL

(75) Inventors: Craig D. Newman, Montvale, NJ (US); Charles G. Hwang, Ridgewood, NJ (US); Richard A. Flowers, Vernon, NJ (US); Glade H. Howell, Sandy, UT (US); Simon Cohn, North Arlington, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 27 days.

(21) Appl. No.: 09/820,571

(22) Filed: Mar. 29, 2001

(65) Prior Publication Data

US 2002/0143352 A1 Oct. 3, 2002

(51) Int. Cl.$^7$ ............................................... A61B 17/32

(52) U.S. Cl. ............................ 606/167; 30/151; 30/335

(58) Field of Search ............................. 606/167, 185, 606/166, 168, 169, 170, 181, 172; 30/151, 335, 2, 158, 167, 539, 162

(56) References Cited

U.S. PATENT DOCUMENTS

| | | | |
|---|---|---|---|
| 2,735,176 A | 2/1956 | Costin | 30/162 |
| 2,885,780 A | 5/1959 | Campbell | 30/164.9 |
| 2,968,489 A | 1/1961 | Doniger | 279/48 |
| 3,025,598 A | 3/1962 | Nissen | 30/162 |
| 3,657,812 A | 4/1972 | Lee | 30/162 |
| 3,793,726 A | 2/1974 | Schrank | 30/151 |
| 3,905,101 A | 9/1975 | Shepherd | 30/162 |
| 3,906,626 A * | 9/1975 | Riuli | 30/162 |
| 4,071,952 A * | 2/1978 | Meshulam et al. | 30/151 |
| 4,091,537 A | 5/1978 | Stevenson, Jr. | 30/286 |
| 4,318,473 A | 3/1982 | Sandel | 206/370 |
| 4,375,218 A | 3/1983 | Di Geronimo | 128/313.17 |
| 4,414,974 A | 11/1983 | Dotson et al. | 128/305 |
| 4,491,132 A | 1/1985 | Aikins | 128/305 |
| 4,523,379 A | 6/1985 | Osterhout et al. | 30/151 |
| 4,576,164 A | 3/1986 | Richeson | 128/305 |
| 4,660,287 A | 4/1987 | Decker | 30/339 |
| 4,664,846 A | 5/1987 | Tkayama | 30/162 |
| 4,735,202 A | 4/1988 | Williams | 128/305 |
| 4,805,304 A | 2/1989 | Knoop | 30/162 |
| 4,823,457 A | 4/1989 | Prochaska | 29/509 |
| 4,844,070 A | 7/1989 | Dee | 128/305 |
| 4,884,569 A | 12/1989 | Fedorov et al. | 128/305 |
| 4,903,390 A | 2/1990 | Vidal et al. | 29/239 |
| 4,949,458 A | 8/1990 | Davis et al. | 30/162 |
| 5,055,106 A | 10/1991 | Lundgren | 606/167 |
| 5,071,418 A | 12/1991 | Rosenbaum | 606/42 |
| 5,071,426 A * | 12/1991 | Dolgin et al. | 606/167 |
| D327,125 S | 6/1992 | Iten | D24/30 |
| 5,141,517 A | 8/1992 | Shutt | 606/167 |
| D330,082 S | 10/1992 | Schutte et al. | D24/147 |
| 5,197,953 A | 3/1993 | Colonna | 604/110 |
| 5,201,748 A | 4/1993 | Newman et al. | 606/167 |
| 5,207,696 A | 5/1993 | Matwijcow | 606/167 |
| 5,250,063 A | 10/1993 | Abidin et al. | 606/167 |
| 5,250,064 A | 10/1993 | Schneider | 606/167 |
| 5,275,606 A * | 1/1994 | Abidin et al. | 606/167 |

(List continued on next page.)

FOREIGN PATENT DOCUMENTS

| | | |
|---|---|---|
| DE | 3722899 A1 | 1/1989 |
| EP | 583 992 A1 | 2/1994 |
| EP | 0 727 186 A2 | 8/1996 |
| EP | 793 943 A1 | 9/1997 |
| WO | WO 97/34535 | 9/1997 |

*Primary Examiner*—John J. Calvert
*Assistant Examiner*—Alissa L. Hoey
(74) *Attorney, Agent, or Firm*—James J. Murtha

(57) ABSTRACT

A shielded surgical scalpel includes an elongate handle defining a longitudinal axis and having a proximal portion and a distal portion. A blade is fixedly attached to the handle. A shield is mounted onto the handle. The shield is movable between a distal position where the shield prevents inadvertent access to the blade and a proximal position where the shield exposes the blade for use.

15 Claims, 10 Drawing Sheets

U.S. PATENT DOCUMENTS

| | | | |
|---|---|---|---|
| 5,292,310 A | 3/1994 | Yoon | 604/158 |
| 5,299,357 A | 4/1994 | Wonderley et al. | 30/339 |
| 5,309,641 A | 5/1994 | Wonderley et al. | 30/339 |
| 5,312,429 A | 5/1994 | Noack | 606/167 |
| 5,330,492 A | 7/1994 | Haugen | 606/167 |
| 5,330,494 A | 7/1994 | van der Westhuizen et al. | 606/167 |
| 5,342,379 A | 8/1994 | Volinsky | 606/167 |
| 5,344,424 A * | 9/1994 | Roberts et al. | 606/167 |
| 5,363,958 A | 11/1994 | Horan | 206/356 |
| 5,370,654 A | 12/1994 | Abidin et al. | 606/182 |
| 5,411,512 A | 5/1995 | Abidin et al. | 606/167 |
| 5,417,704 A | 5/1995 | Wonderley | 606/167 |
| 5,431,672 A | 7/1995 | Cote et al. | 606/167 |
| 5,449,068 A | 9/1995 | Gharibian | 206/355 |
| 5,481,804 A | 1/1996 | Platts | 30/162 |
| 5,496,340 A * | 3/1996 | Abidin et al. | 606/167 |
| 5,571,127 A | 11/1996 | De Campli | 606/167 |
| 5,591,189 A | 1/1997 | Yoon | 606/185 |
| 5,620,454 A | 4/1997 | Pierce et al. | 606/167 |
| 5,662,669 A | 9/1997 | Abidin et al. | 606/167 |
| 5,674,203 A | 10/1997 | Lewandowski | 604/197 |
| 5,683,407 A * | 11/1997 | Jolly et al. | 606/181 |
| 5,741,289 A * | 4/1998 | Jolly et al. | 606/181 |
| 5,752,968 A * | 5/1998 | Jolly et al. | 606/167 |
| 5,792,162 A * | 8/1998 | Jolly et al. | 606/167 |
| 5,827,309 A * | 10/1998 | Jolly et al. | 606/167 |
| 5,868,771 A | 2/1999 | Herbert et al. | 606/167 |
| 5,908,432 A | 6/1999 | Pan | 606/167 |
| 5,938,676 A | 8/1999 | Cohn et al. | 606/167 |
| 5,957,944 A | 9/1999 | Khuri et al. | 606/170 |

* cited by examiner

SHIELDED SURGICAL SCALPEL

BACKGROUND OF THE INVENTION

The field of the invention is surgical cutting instruments. Conventional surgical instruments, e.g. surgical scalpels, provide a significant potential for harm to surgeons, nurses and other medical personnel in a health care facility. In the operating room, various surgical instruments are quickly passed by hand from person to person. The rapid handling of such instruments that have exposed sharp edges can lead to accidental cuts or puncture wounds. Surgical gloves may also be inadvertently punctured leading to loss of glove integrity further increasing the risk of infection to a surgeon, nurse or other medical personnel. Such accidental cuts or puncture wounds are especially problematic because of the advent of currently incurable and/or fatal diseases, such as Acquired Immunosuppressive Deficiency Syndrome ("AIDS") and hepatitis C, which can be transmitted by the exchange of body fluids from an infected person to another person.

Previous attempts to guard against inadvertent cuts or punctures led to the development of various types of shielding mechanisms for blades used on a surgical scalpel. For example, some designs had retractable blades while others had retractable inner or outer shields. Although many different designs were developed, many of these designs had serious drawbacks. Some of the designs required two hands to operate or otherwise were difficult to operate or were easy to defeat.

SUMMARY OF THE INVENTION

It is therefore an object of this invention to provide a shielded surgical scalpel.

It is another object of this invention to provide a shielded surgical scalpel that requires only a single hand to operate and is simple to operate.

It is yet another object of this invention to provide a shielded surgical scalpel that is difficult to defeat.

The shielded surgical scalpel of this invention includes an elongate handle defining a longitudinal axis and having a proximal portion and a distal portion separated by a shoulder. A blade is fixedly attached to the distal portion of the elongate handle. A shield with a proximal end and a distal end is firmly mounted onto the elongate handle and is movable longitudinally along the distal portion of the elongate handle. The shield is movable between a distal position where the shield substantially prevents inadvertent access to the blade and a proximal position where the shield exposes the blade for use. The design of the elongate handle and the shield are such as to provide an intuitive indication to the clinician of the proper operation of the shielded surgical scalpel. In addition, arrows on the elongate handle provide a visual indication to the clinician of the direction the clinician must move the shield in order to shield or expose the blade. Furthermore, a lock indicator line on the distal portion of the elongate handle is aligned with the proximal end of the shield when the shield is locked in the distal position. This provides a visual indication to the clinician that the shield is properly locked and the blade is shielded.

The shield includes an upwardly biased cantilevered digital activation section having at least one inwardly directed boss disposed in a slot formed on the distal portion of the elongate handle. The slot extends generally longitudinally with a proximal upturned end and a distal upturned end. The upturned ends define the proximal most and distal most travel of the shield with respect to the elongate handle. The proximal and distal upturned ends on the elongate handle and the inwardly directed boss on the shield are configured such that they cooperate to tightly hold the shield in the distal or proximal position, as the case may be. The shield is releasable from both the distal position and the proximal position by the downward pressure on the upwardly biased cantilevered digital activation section of the shield, which moves the boss out of the proximal or distal upturned end into alignment with the longitudinal portion of the slot. Once released, the shield can be moved distally or proximally as the case may be to shield or expose the blade.

The shield also includes an inwardly directed lug that engages the surface of the distal portion of the elongate handle. This lug ensures that the shield fits snugly on the elongate handle and prevents undesirable lateral movement of the shield with respect to the elongate handle, especially when the shield is in the proximal position.

The shield and the elongate handle cooperate in such a way that the clinician's glove will not be pinched between the proximal end of the shield and the shoulder separating the proximal portion and the distal portion of the elongate handle when the shield is in the proximal position. The slot defines the length of travel of the shield with respect to the elongate handle. Preferably, the location of the slot and its length are chosen to ensure that there is a gap between the proximal end of the shield and the shoulder on the elongate handle when the shield is in the proximal position.

The shield is configured so that it will not interfere with the blade during use when the shield is in the proximal position. Specifically, the distal bottom edge of the shield is formed with a curve that corresponds to the shape of a standard blade so that a clinician can use the blade at a shallow angle with respect to the patient.

Finally, in order to facilitate the assembly of the shielded surgical scalpel of this invention, a pair of bumps is formed on the external surface of the shield with one bump being located on either side of the shield. These bumps allow the shield to ride on conveyor rails used in the manufacturing process that carry the shield from one station to another.

BRIEF DESCRIPTION OF THE DRAWINGS

The above and other objects and advantages will be apparent upon consideration of the following drawings and detailed description. The preferred embodiments of the present invention are illustrated in the drawings, wherein similar reference numbers denote similar elements throughout the several views and in which.

DETAILED DESCRIPTION OF THE INVENTION

Figure 1:
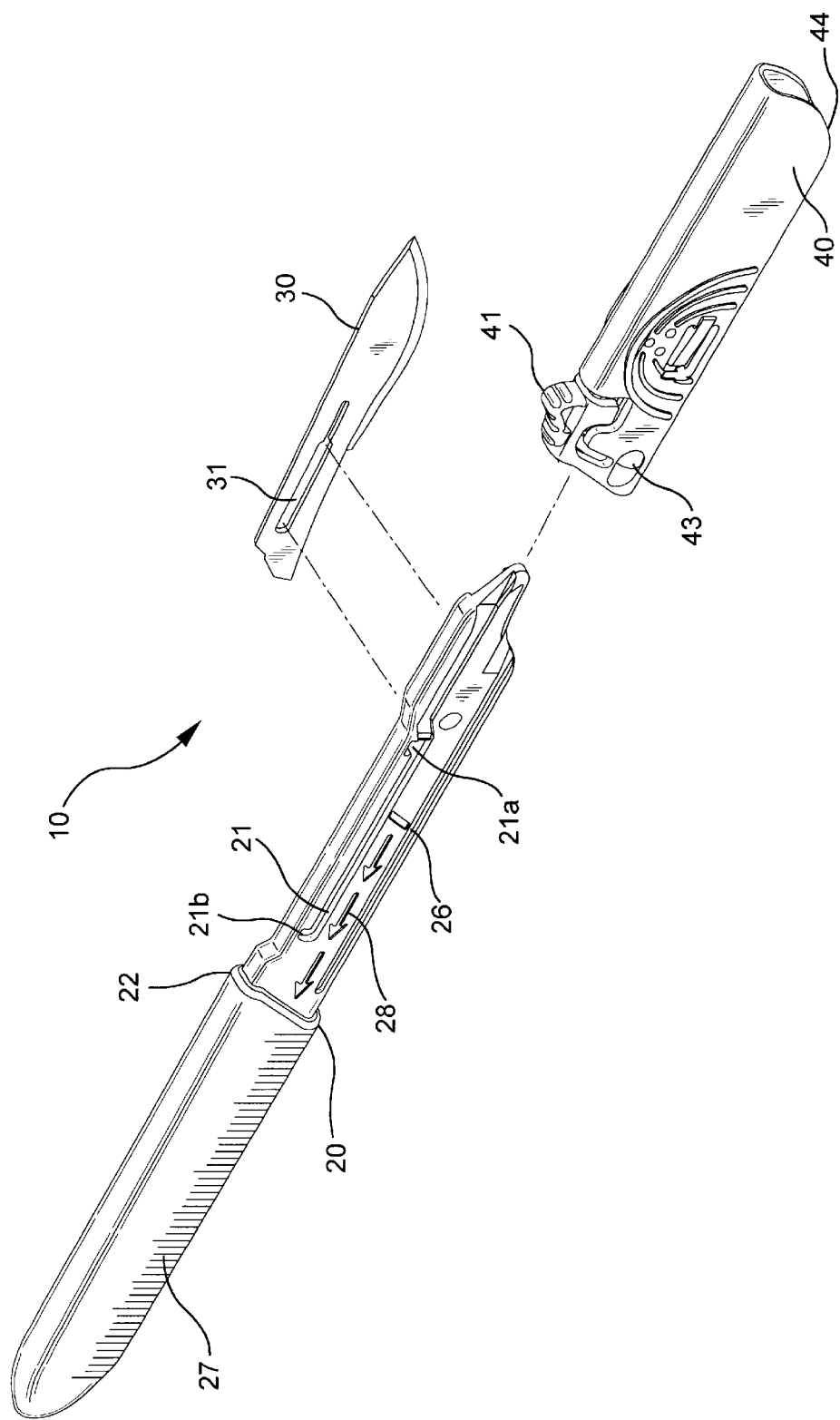
FIG. 1 is an exploded perspective view of a preferred embodiment of the shielded surgical scalpel of this invention.

As used herein, the term "proximal" refers to a location on the shielded surgical scalpel of this invention that, during normal use, is closest to the clinician using the device and farthest from the patient in connection with whom the device is used. Conversely, the term "distal" refers to a location on the shielded surgical scalpel of this invention that, during normal use, is farthest from the clinician using the device and closest to the patient in connection with whom the device is used.

As used herein, the term "top", "up" or "upwardly" refers to a location on the shielded surgical scalpel of this invention that, during normal use, is radially away from the longitudinal axis of the device and away from the patient's skin. Conversely, as used herein, the term "bottom", "down" or "downwardly" refers to a location on the shielded surgical scalpel of this invention that, during normal use, is radially away from the longitudinal axis of the device and toward the patient's skin.

As used herein, the term "in", or "inwardly" refers to a location with respect to the shielded surgical scalpel of this invention that, during normal use, is toward the inside of the device. Conversely, as used herein, the term "out" or "outwardly" refers to a location with respect to the shielded surgical scalpel of this invention that, during normal use, is toward the outside of the device.

A preferred embodiment of the shielded surgical scalpel 10 of the invention is shown generally in the FIGS. Shielded surgical scalpel 10 includes an elongate handle 20 defining a longitudinal axis and has a proximal portion and a distal portion separated by a shoulder 22. The proximal portion of handle 20 may include a scale 27 thereon to aid the clinician during surgical procedures. The distal portion of handle 20 may include arrows 28 thereon to provide a visual indication to the clinician of the direction that the shield, discussed hereinafter, should be moved with respect to handle 20 to expose or shield the blade 30. As shown in the FIGS. arrows 28 point proximally to show the clinician which direction shield 40 must be moved in order to expose blade 30. However, if desired, arrows 28 could point distally or some arrows could point distally while other arrows could point proximally.

Handle 20 may be formed from materials such as polymeric resins or metallic materials. Preferably, handle 20 is formed from a thermoplastic material such as polypropylene, polyethylene, polycarbonate, polysulfone, polyacetal, polyamide and the like. Even more preferably, handle 20 is formed from a glass fiber reinforced nylon material. For example, nylon 6/6 with 10% glass fiber such as provided by LNP Engineering Plastics, Inc. under the Thermocomp® RF-1002 name may be used. If desired, handle 20 may be formed from a metallic material such as formed powdered metal or machined metal. Preferably materials are selected for handle 20 to provide a substantially rigid structure and that are compatible with most sterilization methods.

A blade 30 is fixedly attached to the distal portion of elongate handle 20. Blade 30 is preferably formed from a material such as stainless steel, carbon steel or a ceramic that is suitable for being ground to a sharpened edge for cutting. Blade 30 defines an aperture 31 therein and is fixedly attached to an outward protuberance on handle 20 by fitting aperture 31 over the protuberance. This arrangement ensures that blade 30 is substantially rigid with respect to handle 20. Suitable attachment means include heat staking the protuberance onto aperture 31, adhesive bonding or the like.

Figure 2:
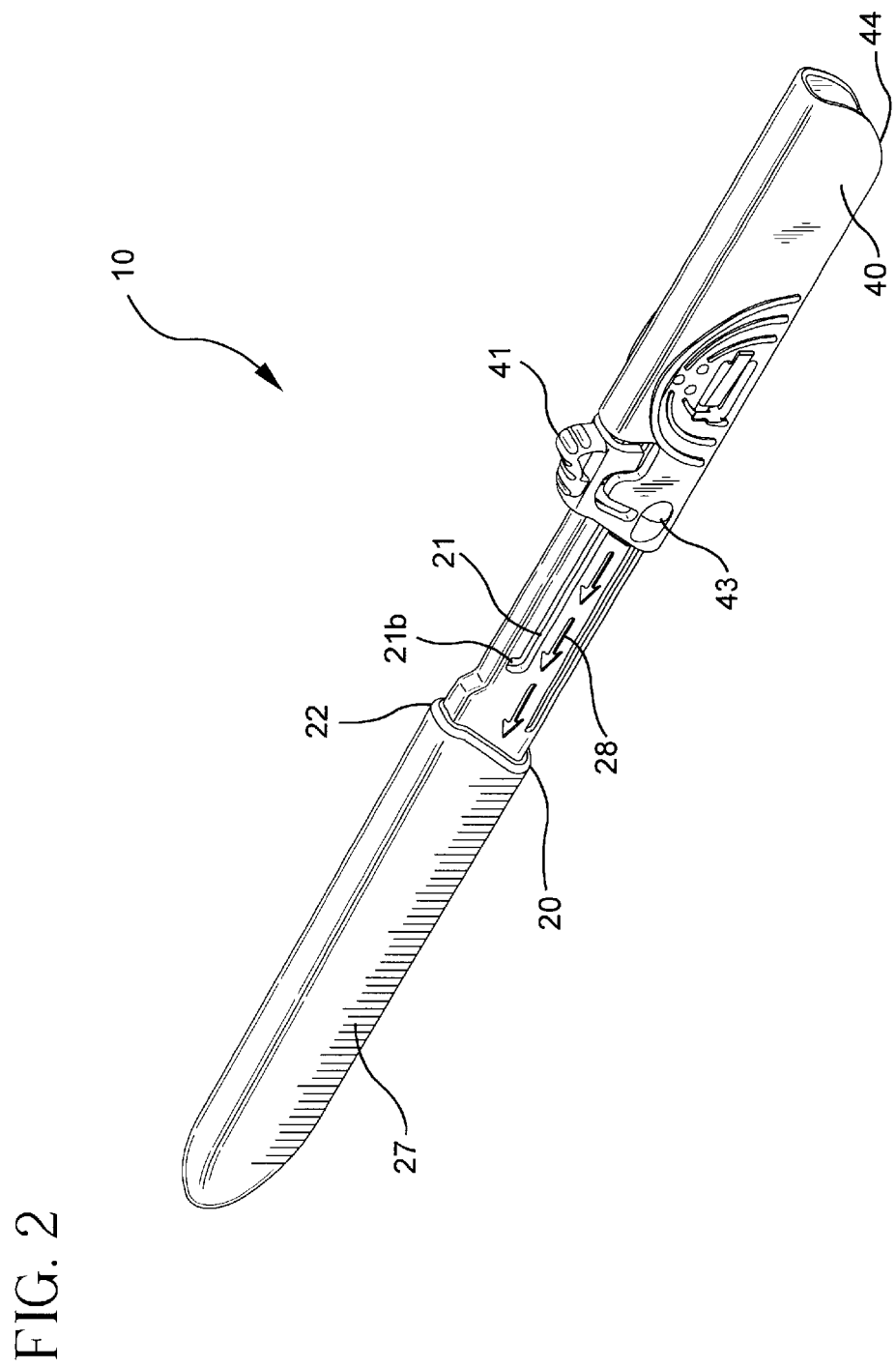
FIG. 2 is a perspective view of the shielded surgical scalpel of this invention with the shield in the distal position preventing inadvertent exposure to the blade.
Figure 3:
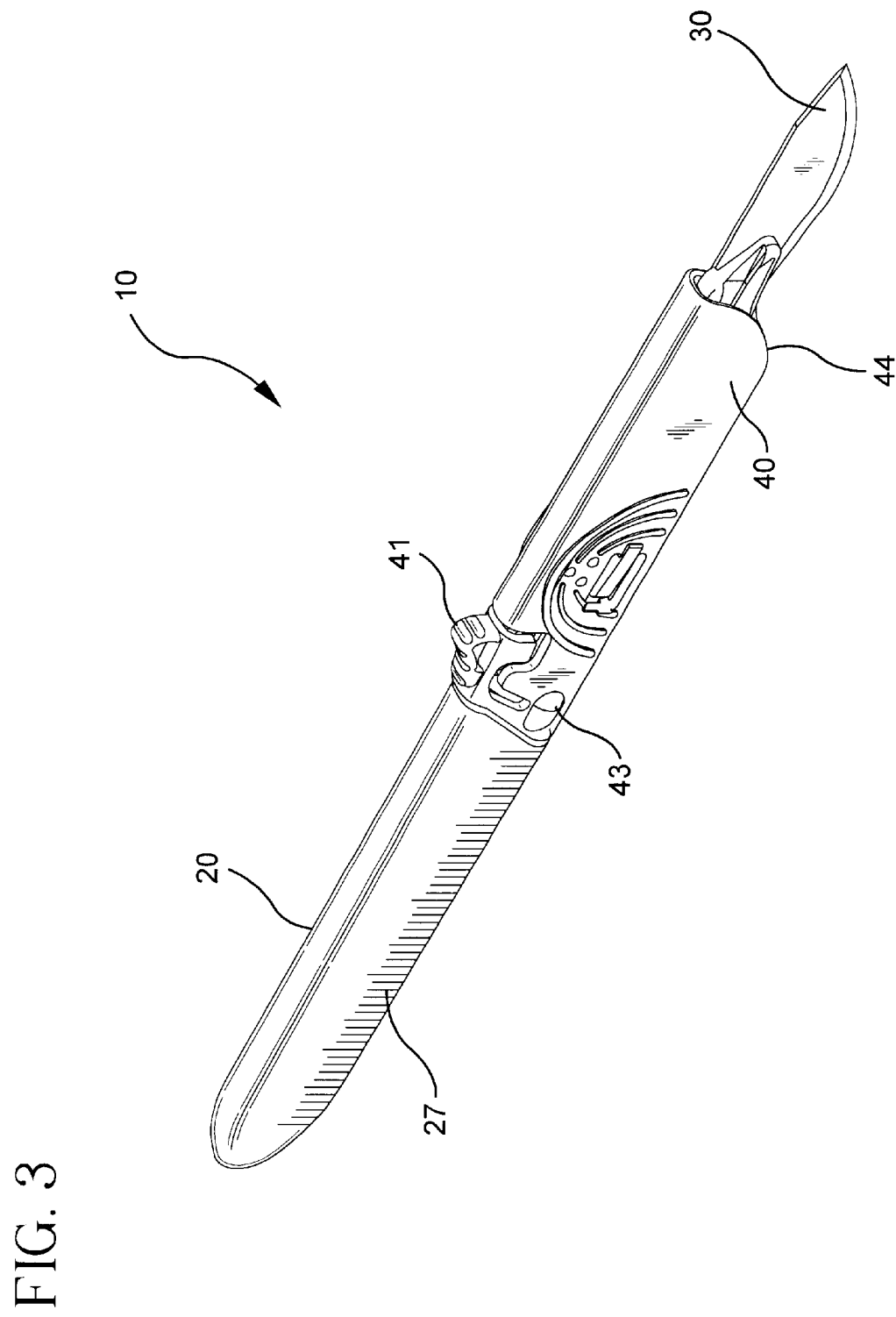
FIG. 3 is a perspective view of the shielded surgical scalpel of this invention with the shield in the proximal position exposing the blade for use.
Figure 4:
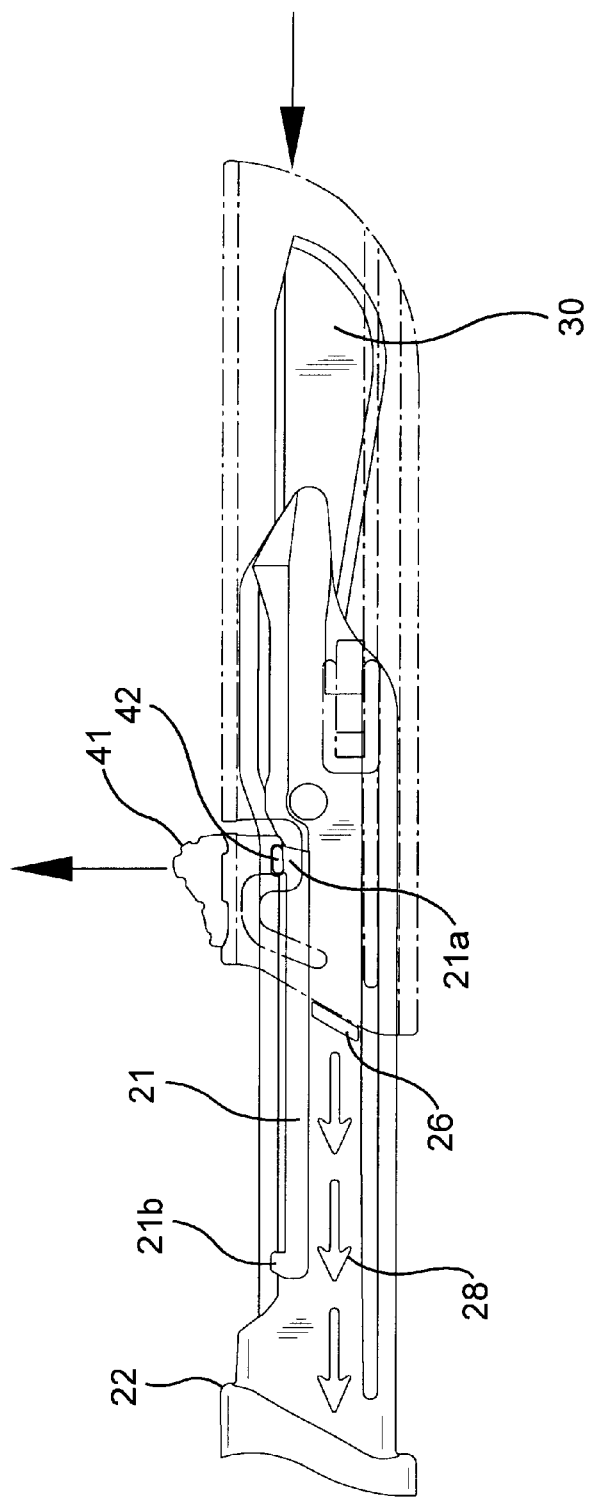
FIG. 4 is a schematic side elevation view of the distal portion of the shielded surgical scalpel of this invention with the shield in phantom in the distal position.
Figure 5:
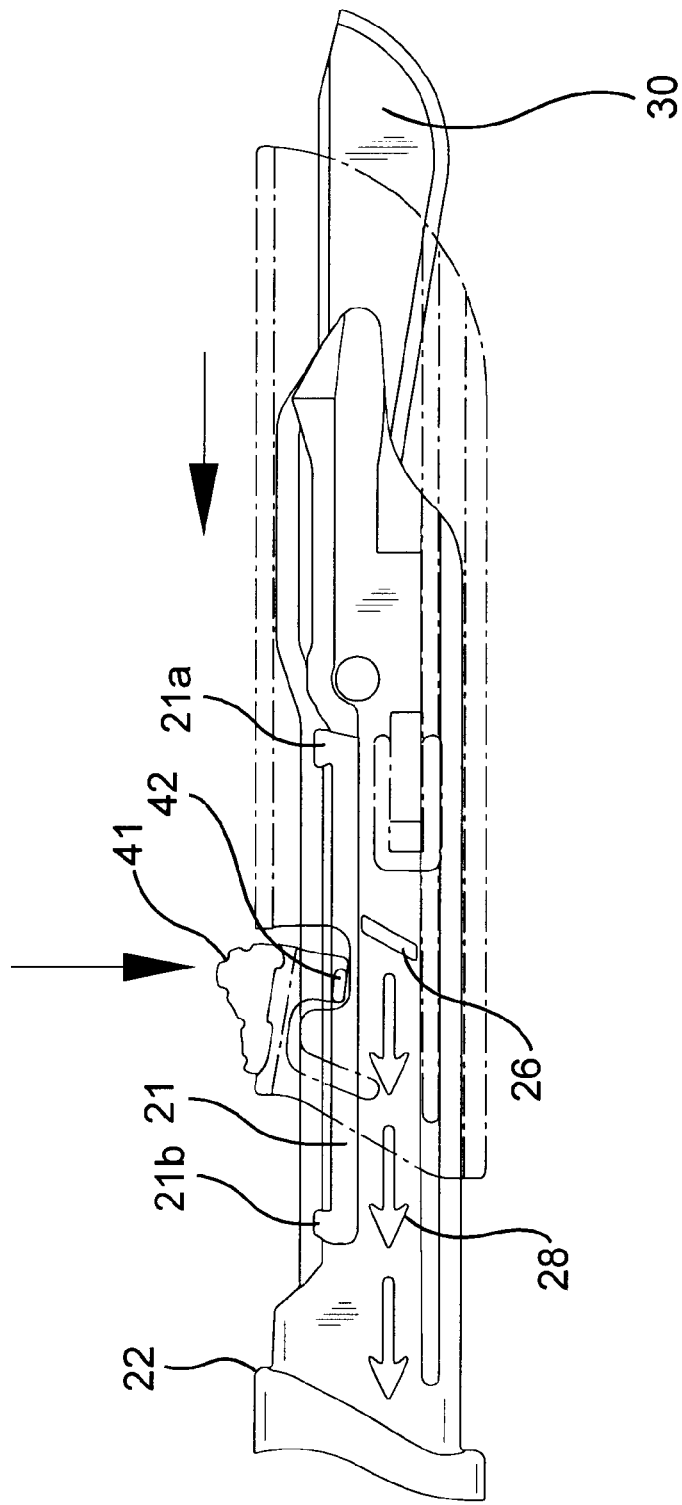
FIG. 5 is a schematic side elevation view of the distal portion of the shielded surgical scalpel of this invention with the shield in phantom between the distal position and the proximal position.
Figure 6:
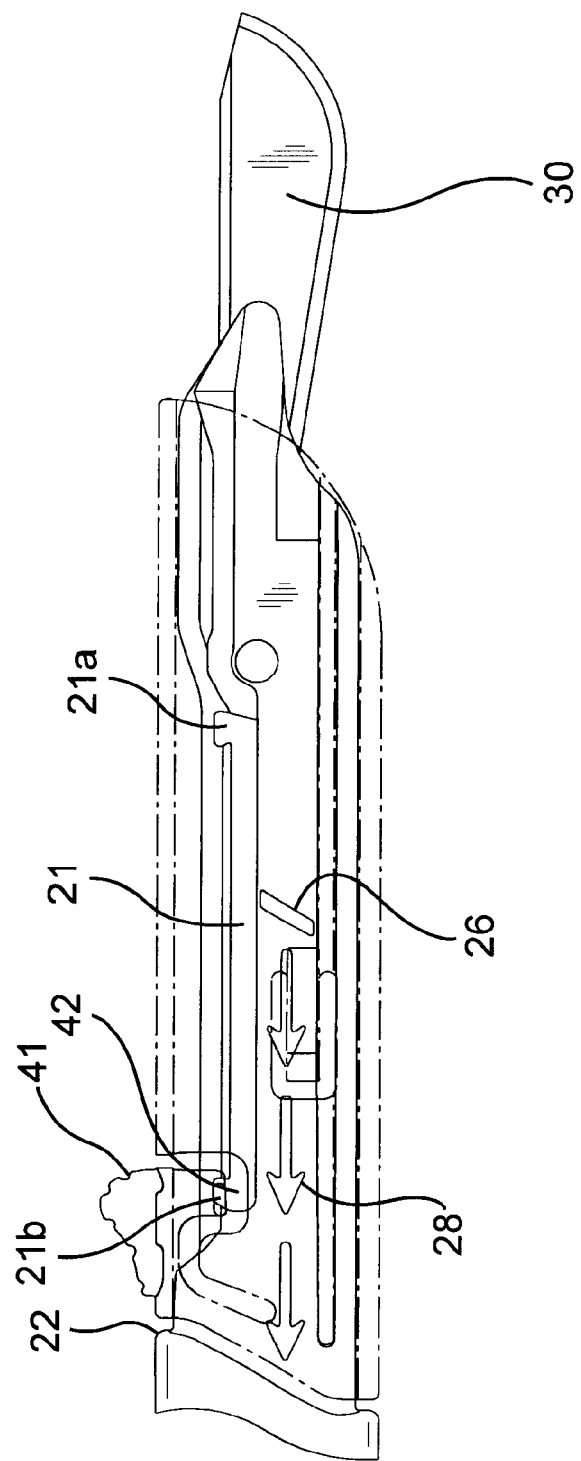
FIG. 6 is a schematic side elevation view of the distal portion of the shielded surgical scalpel of this invention with the shield in phantom in the proximal position.
Figure 7:
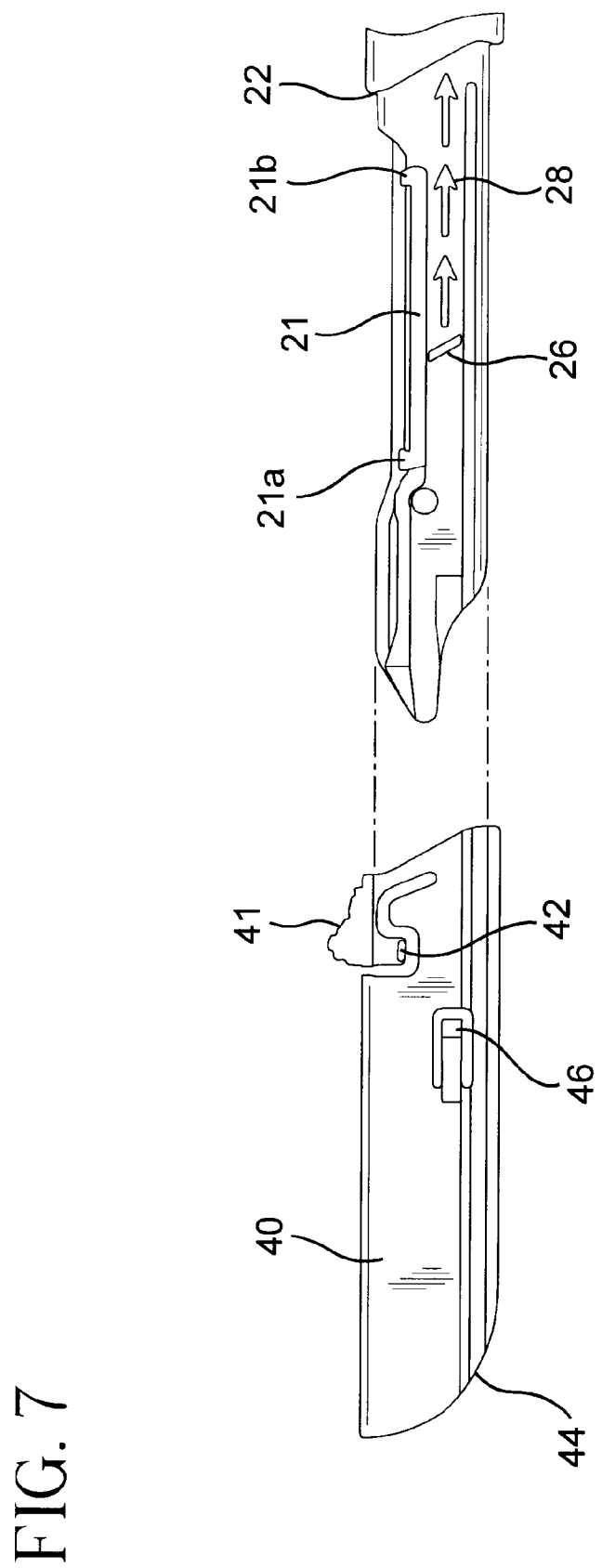
FIG. 7 is a side elevation view of the distal portion of the handle of the shielded surgical scalpel of this invention with no blade and the shield removed.
Figure 8:
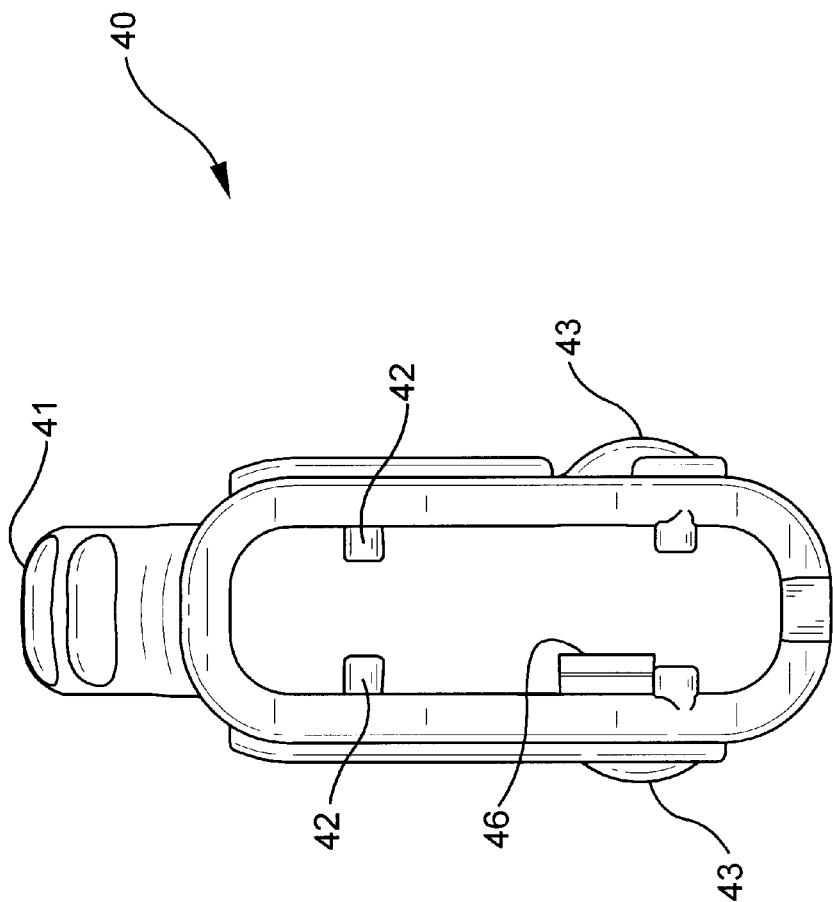
FIG. 8 is an end view of the proximal end of the shield of the shielded surgical scalpel of this invention.

A shield 40 is slidably mounted onto elongate handle 20 for movement between a distal position and a proximal position. In the distal position, best seen in FIG. 2, shield 40 prevents inadvertent access to blade 30. In this position, the proximal end of shield 40 is substantially aligned with a lock indicator line 26 formed on the distal portion of handle 20. Lock indicator line 26 provides a visual indication to the clinician that shield 40 is locked in the distal position with blade 30 shielded by shield 40. In the proximal position, best seen in FIG. 3, shield 40 allows blade 30 to be exposed for use. Preferably, the proximal end of shield 40 does not tightly abut shoulder 22 when shield 40 is in the proximal position. Instead, a gap is located between shoulder 22 and the proximal end of shield 40 when it is in the proximal position. This gap prevents the clinician's glove or skin from being pinched between shoulder 22 and the proximal end of shield 40. Shield 40 may be formed from thermoplastic materials such as polypropylene, polyethylene, polycarbonate, polyacetal, polyamide and the like. For particular applications, the material selected to form shield 40 may be substantially transparent.

Shield 40 includes an upwardly biased cantilevered digital activation section 41 projecting upwardly from the top surface of shield 40. A clinician may apply digital pressure to upwardly biased cantilevered digital activation section 41 sufficient to downwardly deflect digital activation section 41 and release shield 40 for movement between the proximal position and the distal position. Upwardly biased cantilevered digital activation section 41 preferably includes at least one inwardly directed boss 42 designed to cooperate with a slot 21 formed in handle 20 to control movement of shield 40 between the distal position and the proximal position. If two slots are formed in handle 20 on either side thereof, preferably two inwardly directed bosses 42 are formed on cantilevered digital activation section 41.

Slot 21 extends generally longitudinally along the distal portion of handle 20. Slot 21 defines the length of travel of shield 40 with respect to handle 20. Preferably, the location of slot 21 and its length are chosen to ensure that there is a gap between the proximal end of shield 40 and shoulder 22 on handle 20 when shield 40 is in the proximal position. In this way, the gap ensures that the clinician's glove or skin will not be pinched between the proximal end of shield 40 and shoulder 22. Preferably the gap should be about 0.012 inches long. Slot 21 extends between an upturned distal terminus 21a and an upturned proximal terminus 21b. Preferably, handle 20 defines a slot 21 with upturned distal and proximal termini on each side thereof. Boss 42 engages each terminus 21a and 21b when shield 40 is in the distal or proximal position respectively. When boss 42 is engaged in one of the termini, shield 40 is prevented from moving. When the clinician applies sufficient downward force to deflect upwardly biased cantilevered digital activation section 41 so boss 42 is no longer engaged with termini 21a or 21b, the clinician is thereby able to selectively move shield 40 between the proximal and distal positions as desired. Boss 42 tracks in slot 21 to stabilize shield 40 during the movement between the proximal and distal positions. When a terminus is reached, boss 42 serves to provide the clinician with an audibly perceptible sound, such as a "snap" as boss 42 engages the terminus and thus allows upwardly biased cantilevered digital activation section 41 to return to the rest position. This audibly perceptible indication assists the clinician to recognize the completion of the desired movement of shield 40. In addition, the configuration of upwardly biased cantilevered digital activation section 41, boss 42 and termini 21a and 21b provide a tactile indication to the clinician of the completion of the desired movement of shield 40.

Preferably distal terminus 21a is formed such that the proximal edge is tapered rearwardly. This configuration urges boss 42 upwardly into tight engagement with distal terminus 21a if shield 40 were forced rearwardly without depressing upwardly biased cantilevered digital activation section 41. Thus, inadvertent movement of shield 40 from the distal position to the proximal position is minimized. Preferably this taper is on the order of about 60 degrees. In order to maximize the upward movement of boss 42, the proximal edge of boss 42 can also be tapered. Preferably this taper is on the order of about 55 degrees. This taper has a smaller angle to ensure that boss 42 fits fully into distal terminus 21a to ensure that boss 42 is locked in placed therein. In order to ensure that shield 40 is held tightly in place in the distal position, boss 42 should have a longitudinal dimension approximately equal to or slightly less than the longitudinal dimension of distal terminus 21a. In order to ensure that shield 40 is held tightly in place in the proximal position, boss 42 should have a longitudinal dimension approximately equal to or slightly less than the longitudinal dimension of proximal terminus 21b. Preferably the longitudinal dimension of proximal terminus 21b is the same as the longitudinal dimension of distal terminus 21a.

Preferably, shield 40 includes an inwardly projecting lug 46 disposed to slidably engage the external surface of the distal portion of handle 20. The engagement of lug 46 with the surface of handle 20 provides stability to shield 40 during movement between the proximal and distal positions. In addition, lug 46 ensures that shield 40 fits snugly on handle 20 and prevents undesirable lateral movement of shield 40 with respect to handle 20, especially when shield 40 is in the proximal position. This improves the overall rigidity and feel of shielded surgical scalpel 10 in the clinician's hand.

Figure 9:
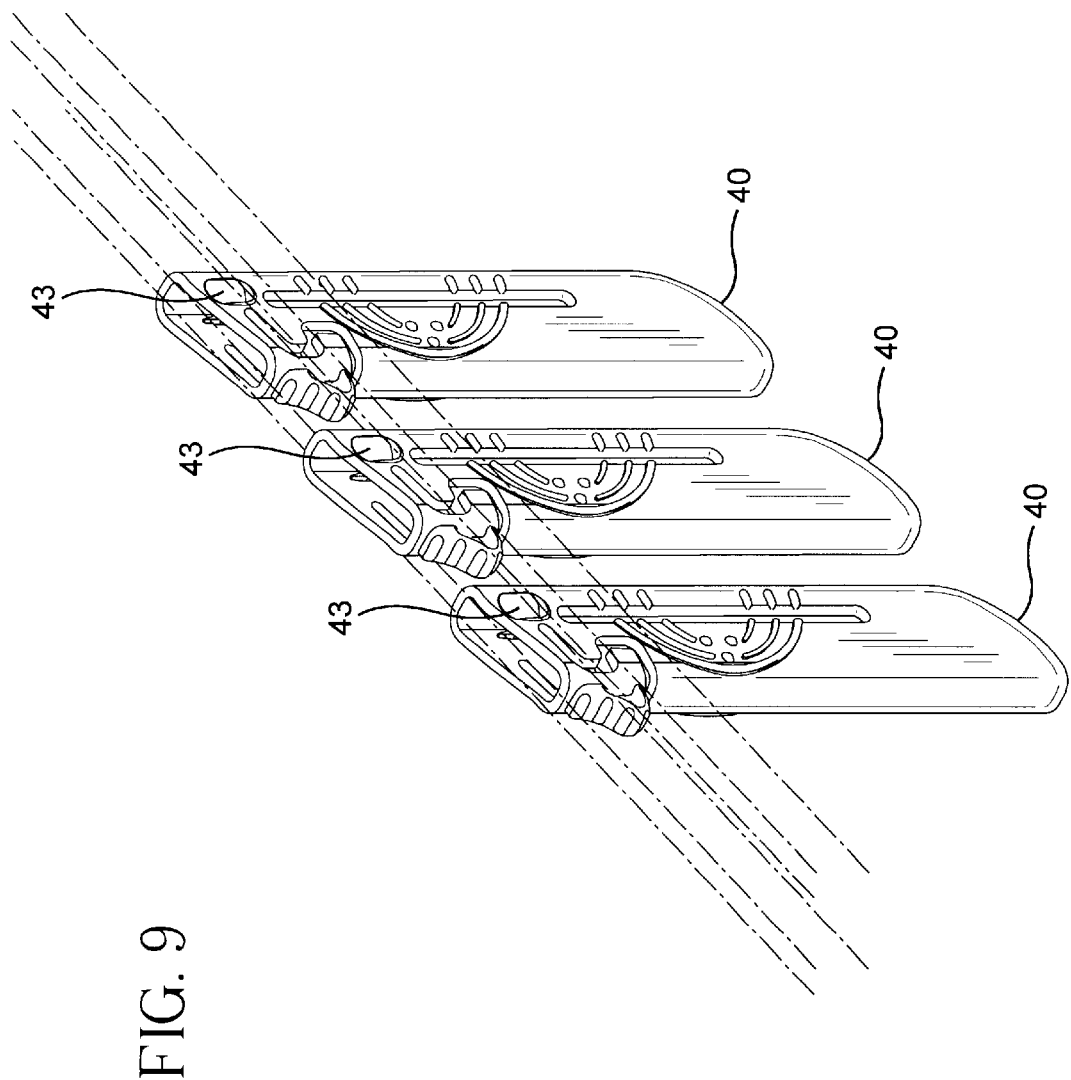
FIG. 9 is a perspective view of a plurality of shields for use with the shielded surgical scalpel of this invention on a pair of conveyor rails shown in phantom.
Figure 10:
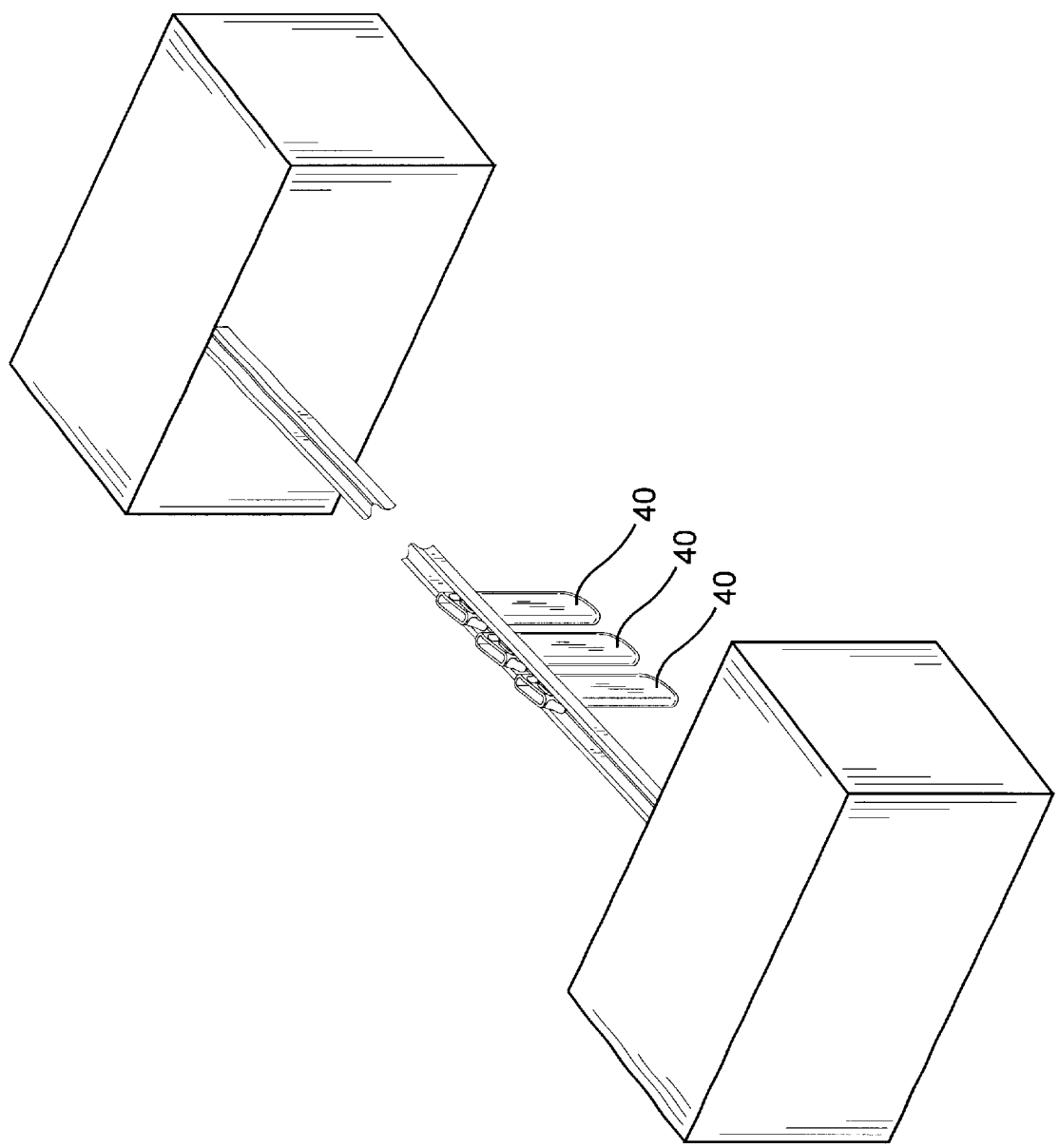
FIG. 10 is a schematic view of a plurality of shields for use with the shielded surgical scalpel of this invention on a pair of conveyor rails that transport the shields between two stations in the manufacturing process.

Preferably, shield 40 also includes outwardly extending bumps 43 to facilitate manipulation of shield 40 during the process for manufacturing shielded surgical scalpel 10. Bumps 43 allow shield to be carried by conveyor rails between different stations during a manufacturing process. See FIGS. 9 and 10. Although bumps 43 can be located anywhere on the exterior of shield 40, bumps 43 should be located toward one end of shield 40. However, preferably bumps 43 are located on either side of shield 40 adjacent to the proximal end thereof. Bumps 43 can have any configuration that allows shield 40 to be carried by the conveyor rails. However, bumps 43 preferably extend about 0.03 inches above the surface of shield 40, have a minor axis of about 0.12 inches, a major axis of about 0.21 inches and a rounded outer surface Preferably, the bottom distal edge 44 of shield 40 is formed in such a manner that it does not interfere with the cutting edge of blade 30 during use yet covers the cutting edge of blade 30 when shield 40 is in the distal position. Preferably, bottom distal edge 44 of shield is formed from a curve defined by a radius of 0.55 inches to correspond to the shape of a standard blade. By tapering this edge of shield 40 in the proper configuration, the clinician can use shielded surgical scalpel 10 of this invention at a shallow angle in the same manner that a conventional surgical scalpel can be used.

Thus, it is seen that a shielded surgical scalpel is provided that requires only one hand to operate and is otherwise easy to operate but is difficult to defeat. While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents.

What is claimed is:

1. A shielded surgical scalpel comprising:

an elongate handle formed as a solid body having a proximal portion and a distal portion, wherein the handle defines a slot formed thereon with a distal upturned terminus having a tapered proximal edge and a proximal upturned terminus;

a blade fixedly attached to the handle;

a shield mounted onto the handle surrounding the handle at least in part and being movable between a distal position wherein the shield substantially prevents inadvertent access to the blade and a proximal position wherein the shield allows the blade to be exposed for use wherein the shield includes an upwardly biased cantilevered digital activation section having an inwardly directed boss disposed in the slot.

2. The shielded surgical scalpel of claim 1 wherein the tapered proximal edge of the distal upturned terminus has a taper of about 60 degrees.

3. The shielded surgical scalpel of claim 1 wherein the boss includes a tapered proximal edge.

4. The shielded surgical scalpel of claim 3 wherein the tapered proximal edge of the boss has a taper of about 55 degrees.

5. A shielded surgical scalpel comprising:

an elongate handle having a proximal portion and a distal portion with a shoulder defined therebetween, wherein the handle defines a slot formed thereon with a proximal upturned terminus and a distal upturned terminus;

a blade fixedly attached to the handle;

a shield mounted onto the handle and being movable between a distal position wherein the shield prevents inadvertent access to the blade and a proximal position wherein the shield allows the blade to be exposed for use wherein the shield includes an upwardly biased cantilevered digital activation section having an inwardly directed boss disposed in the slot and wherein the shield includes a proximal edge and a gap is defined between the proximal edge of the shield and the shoulder when the shield is in the proximal position.

6. A shielded surgical scalpel comprising:

an elongate handle having a proximal portion and a distal portion with a shoulder defined therebetween, wherein the handle defines a slot formed thereon with a proximal upturned terminus and a distal upturned terminus;

a blade fixedly attached to the handle;

a shield having a proximal end and being mounted onto the handle and movable between a distal position wherein the shield prevents inadvertent access to the blade and a proximal position wherein the shield allows the blade to be exposed for use wherein the shield includes an upwardly biased cantilevered digital activation section having an inwardly directed boss disposed in the slot and wherein the distal portion of the elongate handle includes a visual indication of the operation of the shield.

7. The shielded surgical scalpel of claim 6 wherein the visual indication of the operation of the shield is a lock indicator line disposed on the distal portion of the handle that is aligned with the proximal end of the shield when the shield is in the distal position to indicate that the shield is in the distal position.

8. The shielded surgical scalpel of claim 6 wherein the visual indication of the operation of the shield is at least one arrow disposed on the distal portion of the handle that points either proximally or distally.

9. A shielded surgical scalpel comprising:

an elongate handle having a proximal portion and a distal portion with a shoulder defined therebetween, wherein the handle defines a slot formed thereon with a proximal upturned terminus and a distal upturned terminus;

a blade fixedly attached to the handle;

a shield having a bottom distal edge and being mounted onto the handle and movable between a distal position wherein the shield prevents inadvertent access to the blade and a proximal position wherein the shield allows the blade to be exposed for use wherein the shield includes an upwardly biased cantilevered digital activation section having an inwardly directed boss disposed in the slot and wherein the bottom distal edge of the shield defines a curve that corresponds to the curve of a standard blade.

10. A shielded surgical scalpel comprising:

an elongate handle having a proximal portion and a distal portion with a shoulder defined therebetween, wherein the handle defines a slot formed thereon with a distal upturned terminus having a tapered proximal edge and a proximal upturned terminus;

a blade fixedly attached to the handle;

a shield having a proximal end and a bottom distal edge mounted onto the handle and movable between a distal position wherein the shield prevents inadvertent access to the blade and a proximal position wherein the shield allows the blade to be exposed for use wherein the shield includes an upwardly biased cantilevered digital activation section having an inwardly directed boss disposed in the slot and wherein the distal portion of the elongate handle includes a visual indication of the operation of the shield and a gap is defined between the proximal end of the shield and the shoulder when the shield is in the proximal position and wherein the bottom distal edge of the shield defines a curve corresponding to the curve of a standard blade.

11. The shielded surgical scalpel of claim 10 wherein the tapered proximal edge has a taper of about 60 degrees.

12. The shielded surgical scalpel of claim 10 wherein the boss includes a tapered proximal edge.

13. The shielded surgical scalpel of claim 12 wherein the tapered proximal edge of the boss has a taper of about 55 degrees.

14. The shielded surgical scalpel of claim 10 wherein the visual indication of the operation of the shield is a lock indicator line disposed on the distal portion of the handle that is aligned with the proximal end of the shield when the shield is in the distal position to indicate that the shield is in the distal position.

15. The shielded surgical scalpel of claim 10 wherein the visual indication of the operation of the shield is at least one arrow disposed on the distal portion of the handle that points either proximally or distally.

* * * * *